(12) United States Patent
Groman (10) Patent No.: US 6,347,984 B1
(45) Date of Patent: Feb. 19, 2002

(54) MICRO ABRASIVE BLASTING DEVICE AND METHOD

(76) Inventor: Barry Boaz Groman, 1917 NW. 80 Ave., Margate, FL (US) 33063

( * ) Notice: Subject to any disclaimer, the term of this patent is extended or adjusted under 35 U.S.C. 154(b) by 0 days.

(21) Appl. No.: 09/702,270

(22) Filed: Oct. 30, 2000

(51) Int. Cl.[7] .................................................. B24C 7/00
(52) U.S. Cl. ........................... 451/90; 451/102; 451/99
(58) Field of Search ............................ 451/38, 39, 101, 451/102, 90, 99, 75

(56) References Cited

U.S. PATENT DOCUMENTS

| | | |
|---|---|---|
| 2,441,441 A | 5/1948 | Paasche |
| 4,475,370 A | 10/1984 | Stark et al. |
| 5,839,946 A | 11/1998 | Reuben et al. |
| 6,004,191 A | 12/1999 | Schur et al. |

*Primary Examiner*—Derris H. Banks (57) ABSTRACT

The present invention is a superior micro abrasive blasting device (55) with an integral sealed reservoir (22) that converts into a mixing chamber (23). When not in use, the micro abrasive blasting device (55) forms a sealed reservoir (22) that protects the stored particulate matter (20) from contamination and spillage. When the device is setup for use, the sealed reservoir (22) transforms into an operational mixing chamber (23). A method is provided for easily unsealing reservoir (22) and turning it into the mixing chamber (23) in a single motion. In the preferred embodiment, a compliant closure cap (30) is displaced along the container side wall (15) in the direction of the container end wall (17) . The displacement causes the gas-delivery conduit (25) disposed within the reservoir (22) to protrude through the compliant closure cap (30) and to form a gas-receiving port (35). The same displacement to the closure cap (30) removes the discharge conduit cap (67) internal to the sealed reservoir (22), opening the discharge conduit inlet (12) for particulate matter (20) passage. The position of closure cap (30) with respect to the discharge conduit inlet (12) provides means for gas-abrasive flow regulation.

19 Claims, 9 Drawing Sheets

MICRO ABRASIVE BLASTING DEVICE AND METHOD

BACKGROUND OF THE INVENTION

The present invention relates generally to the field of devices for propelling particulate matter with intent to etch the surface of a target material. More specifically, the present invention relates to a micro abrasive blasting device with a sealed reservoir powered by a pressurized-gas source for use with dental procedures.

There are many devices and methods for impacting the surface of a target material with particulate matter. Devices of many sizes and types are available for this process, and many types of pressurized gases such as air, nitrogen, oxygen, and others power them. These devices operate on the physical property that gas at higher pressure flows towards and into gas at lower pressure. When particulate matter is mixed with gas at higher pressure, the gas carries the particulate matter as the gas accelerates and flows to the lower pressure. As the gas and particulate matter blast the target material at high speed, the impact of the particles removes layers of the target material.

This process of material removal is commonly known as etching and also as sandblasting. As the rate of the target material removal increases, the etching process can be utilized for drilling and cutting. More specifically, the aggressiveness of the particulate impact-speed and frequency determine the rate of material removal, and thus whether an abrasive blasting device is useful for polishing, etching, or drilling. Particulate impact-speed and frequency are adjusted by variation of the gas flow rate and gas-to-particulate mixture ratio.

The aggressiveness of the etching process is also a function of the particulate matter. Specific to dentistry, hard aluminum oxide particles are normally utilized for etching and cutting, while softer particles such as sodium bicarbonate are used for cleaning and polishing. Other types of particulate materials with various harnesses are used to achieve various operational objectives.

In dentistry this technology is known as micro-abrasion and is used to achieve a variety of goals—such as to remove foreign material or to dull a shiny surface, roughen or etch the surface to enhance bonding quality, and to remove decay by drilling and cutting tooth structure. Micro-abrasive blasting devices for dental applications strive to utilize particulate materials with small particle diameters. Smaller particles provide finer micro-pores and less discomfort to the patient. More refined particulate materials also wash quicker and easier from the mouth, again adding to patient comfort level. The major problem with using finer particulate matter is their higher sensitivity to moisture. Moisture in fine particulate matter causes the particles to clump together thus changing their flow properties.

Some etching devices compensate for variation in flow properties by adding mechanisms that remove moisture or clear clumped particles in order to facilitate consistent mixing action. Other devices use mechanical agitation and complex plumbing to facilitate mixing of the gas and abrasive particles. These devices also use various forms of flow control.

One device that provides adjustable flow control is the Paasche device, U.S. Pat. No. 2,441,441. The Paasche device is still widely used by dentists. The device utilizes a screw mounted into the reservoir closure cap to regulate the amount of abrasive contained in the air stream. The screw is manually adjusted to regulate the gas-abrasive mixture by providing means for varying the gap between the screw tip and gas-abrasive exit tube.

The mixing method utilized by Stark et al., U.S. Pat. No. 4,475,370, Hertz, U.S. Pat. No. 5,839,946, and Schur et al. U.S. Pat. No. 6,004,191, provides a simple device with no moving parts and a single mixing chamber.

The mixing chamber has only one port for pressurized gas delivery and only one discharge port for gas-particulate mixture release.

The Stark et al. device was designed to operate in the dental lab for material preparation. Stark et al. makes the device refillable by providing a closure cap carrying a gas-delivery conduit for replenishing the device with abrasive material for repeated use. Hertz and Schur et al. disclose the use of a pre-filled and sealed particulate-mixing chamber. The Hertz and Schur et al. design hinder particulate contamination in order to create a device suitable for intra-oral use, by forming a single-use device that can not be readily refilled once the particulate matter is depleted.

The invention disclosed herein solves multiple significant shortcomings with the Stark et al., Hertz, and Schur et al. devices that use this mixing method.

(a) Their first shortcoming is due to the physical properties of the abrasive material in the reservoir.

(I) The gas-delivery conduit carried by the closure cap of the Stark et al. device is difficult to push into the reservoir during cap closure. It is especially difficult when the reservoir contains hard abrasive particles. The resistance of the particulate matter against the gas-delivery conduit during the closure of the reservoir cap causes the gas-delivery conduit to deform as it is inserted. Deformation such as bending may cause the gas-delivery conduit to change the direction of the delivered gas, thus changing the mixing pattern and reducing the effectiveness of the device operation.

(II) It is also likely that during the insertion of the gas-delivery conduit, abrasive particles would get jammed in the gas-delivery conduit, thus causing a restriction in the conduit delivering gas into the device. Both Hertz and Schur et al. experience this same difficulty as they insert the gas-delivery conduit into the mixing chamber during the assembly process of their devices. Since their devices are pre-filled and sealed, testing for this assembly failure can not be performed. This means that the user discovers this defect at time of use.

(b) A second shortcoming is that when the particulate matter is poured into the Stark et al. device some abrasive material enters the discharge conduit and exits the device. This restricts the locations where the device can be refilled, since the abrasive particles are very damaging to mechanical equipment, work surfaces, and are not very pleasant to the touch. Again, both Hertz and Schur et al. experience this same difficulty as they fill their devices with measured amounts of particulate matter during the assembly process.

(c) A third shortcoming solved by the present invention is due to the sensitivity of the abrasive particles to moisture in the atmosphere. Moisture in the air causes the abrasive particles to stick together thus reducing the mixing efficiency of the device. This leads to the potential clogging of the discharge conduit during operation. Therefore, if the Stark et al. device is not used immediately after the reservoir is replenished with dry particulate matter, there is the potential for degradation in performance or failure of the device to operate due to moisture.

Hertz recognizes the moisture and contamination issue. Hertz discloses an inlet cap for sealing the gas-receiving port and a tip cap for sealing the distal end of the particle-directing tube external to the chamber. Since Hertz's tip cap resides on the distal end of the particle-directing tube external to the chamber, during the abrasive filling operation or movement of the device prior to use, abrasive material travels into the discharge conduit. This trapped abrasive material can not be removed from the discharge conduit prior to use by turning the device over, since the abrasive material internal to the chamber blocks the discharge conduit inlet.

Some of this trapped abrasive material spills out of the discharge conduit when the tip cap is removed from the Hertz device. However, some of the abrasive material trapped in the discharge conduit compacts and clumps inside the discharge conduit. In some instances this trapped material may obstruct the discharge conduit and prevent the device operation. In other instances the clumped material is released when pressurized-gas is first applied to the device. Since the abrasive particles in the discharge conduit do not go through the mixing chamber, the initial pressurized-gas application causes the trapped abrasive to be released in a dense clump. This abrasive clump release causes an initial puff of abrasive that is inconsistent with the normal pace of particulate delivery during the device operation. This initial blast of abrasive may also damage the target surface by over etching.

(d) A fourth shortcoming is the risk of utilizing a tip cap for sealing the distal end of the particle-directing tube external to the chamber. Failure of the user to manually remove the Hertz tip cap prior to application of pressurized-gas, could result in the tip cap becoming a dangerous projectile as the gas-particulate stream propels it. The tip cap is especially a liability when the Hertz and Schur et al. devices are used on patients.

(e) A fifth shortcoming is the use of removable inlet and tip caps by Hertz.

(I) The need to remove the caps prior to use significantly inconveniences the user—dentist or dental assistant—which profits by rapidly completing a procedure.

(II) The caps are a liability, since during the removal of the caps in preparation for use, there is the potential of misplacing a cap. Since the patient may be already in the dental chair with the mouth open, any loose components must be carefully accounted for.

(f) A sixth and major drawback of these devices is that no mechanism for regulating the gas-abrasive mixture is provided. The implication of this drawback is that multitudes of devices must by configured to achieve various operational ranges of gas-abrasive mixtures and flow rates. Such configurations provide devices with gas-abrasive flows that are individually optimized for specific use. Physical device configurations range from light gas-abrasive flow for light etching to aggressive gas-abrasive flow that is sufficient for drilling and cutting.

BRIEF SUMMARY OF THE INVENTION

Accordingly, several objects and advantages of the present invention are:

(a) to provide a device with more consistent operation by eliminating the potential for deformation of the gas-delivery conduit during cap closure.

(b) to provide a more reliable device by eliminating the potential for clogging of the gas-delivery conduit during gas-delivery conduit insertion.

(c) to provide a device that is not messy to fill by eliminating spillage of abrasive through the discharge conduit.

(d) to provide a device with better operational performance by eliminating the potential for abrasive material to accumulate in the discharge conduit.

(e) to provide a more reliable device by eliminating the potential for abrasive material to obstruct the discharge conduit.

(f) to provide a device that is safer to use by eliminating the potential for the tip cap to dislodge off the particle-directing tube when pressurized-gas is applied.

(g) to provide a device that is safer and more convenient to use by eliminating the need for the user to remove caps prior to operation.

(h) to provide a device with a sealed abrasive reservoir that unseals in a single motion as the pressurized-gas delivery connector is attached to the device.

(i) to provide a device with means for regulating the gas-abrasive flow, so a single device is able to operate in a wide range of applications, from light etching to drilling and cutting.

BRIEF DESCRIPTION OF THE SEVERAL VIEWS OF THE DRAWING

Various other objects, advantages, and features of the invention will become apparent to those skilled in the art from the following discussion taken in conjunction with the following drawings, where closely related figures have the same number but different alphabetic suffixes:

FIGS. 6A & 6B; FIGS. 7A & 7B; FIGS. 8A & 8B.

REFERENCE NUMERALS IN DRAWINGS 10 discharge conduit
12 discharge conduit inlet 14 container
15 container side wall
17 container end wall
20 particulate matter
22 reservoir
23 mixing chamber
25 gas-delivery conduit
30 closure cap
35 gas-receiving port
40 gas-receiving port cap
45 discharge port
50 particle-directing tube
55 micro abrasive blasting device
65 discharge conduit cap mechanism
67 discharge conduit cap
70 regulator markings

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

Figure 1A:
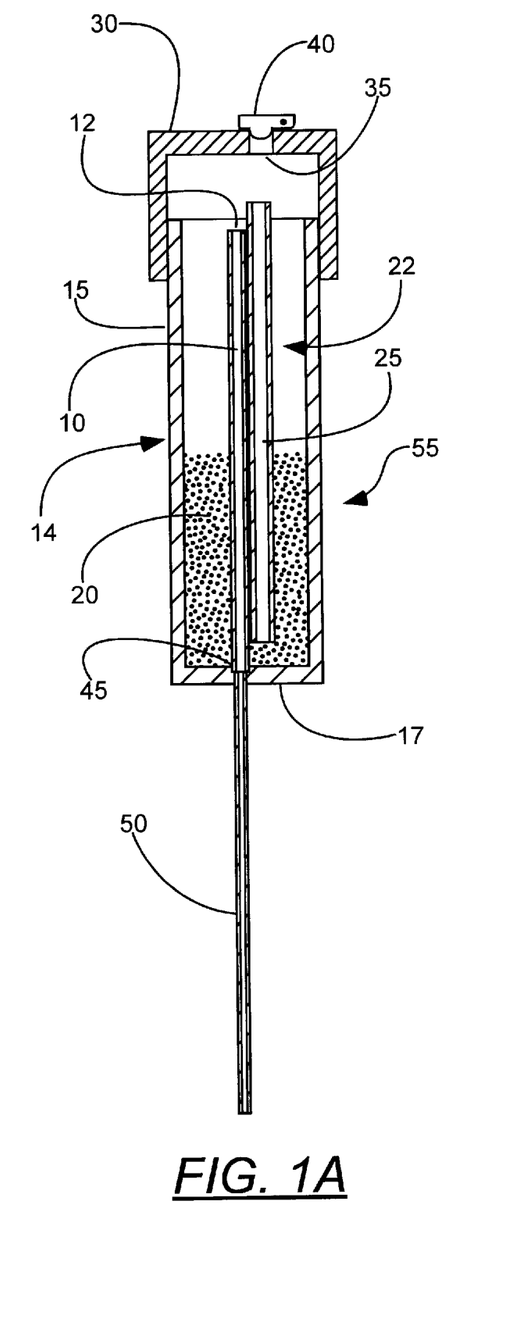
FIGS. 1A & 1B are a cross-sectional side view of the micro abrasive blasting device. The pressurized-gas source is omitted.

Referring to FIG. 1A, a micro abrasive blasting device 55 is disclosed. The micro abrasive blasting device 55 includes container 14 having a container side wall 15 and a container end wall 17. A closure cap 30 is disposed at the open end of container 14. A discharge port 45 is disposed in container end wall 17. A discharge conduit 10 extends in fluid communication from discharge port 45 into container 14. A particle-directing tube 50 is provided in fluid communication with discharge port 45 and extends opposite discharge conduit 10 external to container 14. A gas-delivery conduit 25 is disposed within container 14, with one end directed towards closure cap 30 and the other end directed towards container end wall 17. A gas-receiving port 35 is disposed in closure cap 30. A gas-receiving port cap 40 blocks gas-receiving port 35 to seal closure cap 30.

In the preferred embodiment, gas-delivery conduit 25 is attached to or supported by discharge conduit 10. Gas-delivery conduit 25 can be attached to discharge conduit 10 with adhesives, fasteners, or extruded (or molded) as a single contiguous piece with discharge conduit 10. In addition, gas-delivery conduit 25 can also be supported by container side wall 15 or container end wall 17 via a fastener(s) or a support feature(s) built into container 14. Gas-delivery conduit 25 could also be molded as a single contiguous piece with container side wall 15, container end wall 17, or both. Of course, gas-delivery conduit 25 could also be positioned between discharge conduit 10 and container side wall 15, including abutting container side wall 15.

Figure 1B:
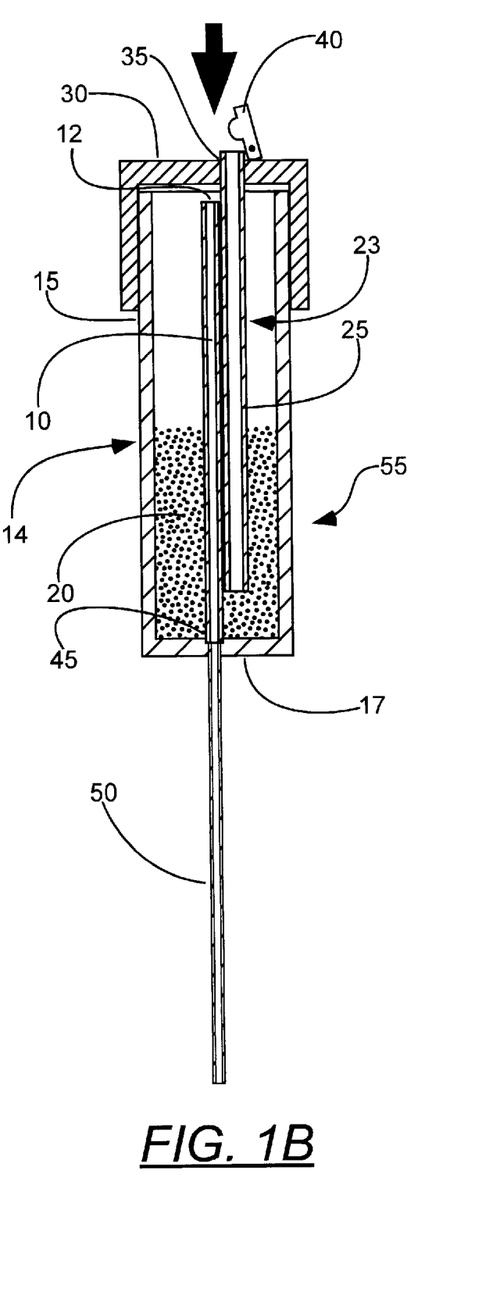

Referring to FIG. 1B, the positioning of closure cap 30 so gas-delivery port cap 40 is pushed out of gas-receiving port 35, permits gas-delivery conduit 25 to be in fluid communications with gas-receiving port 35. The change in closure cap 30 position transforms reservoir 22 into functional mixing chamber 23, by providing means for pressurized-gas to be delivered into mixing chamber 23.

Figure 2A:
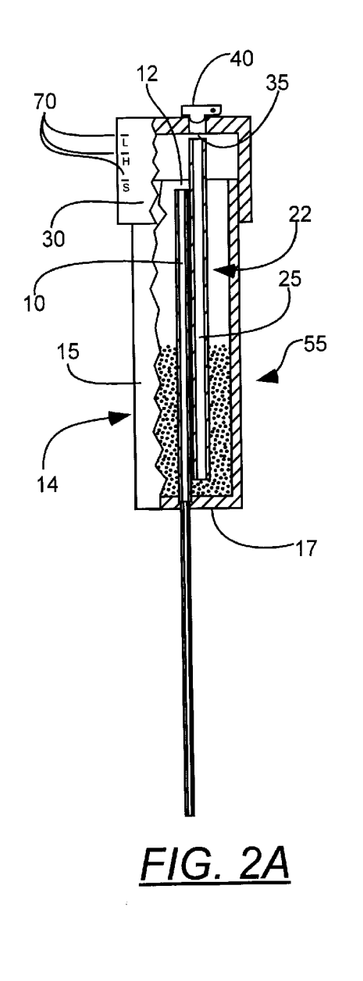
FIGS. 2A–C are a cross-sectional side view of the micro abrasive blasting device, where closure cap positioning provides means for gas-abrasive flow regulation. The pressurized-gas source is omitted.
Figure 2B:
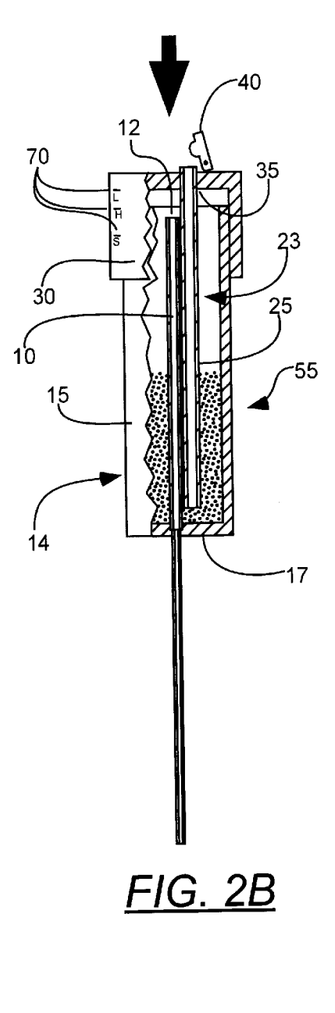
Figure 2C:
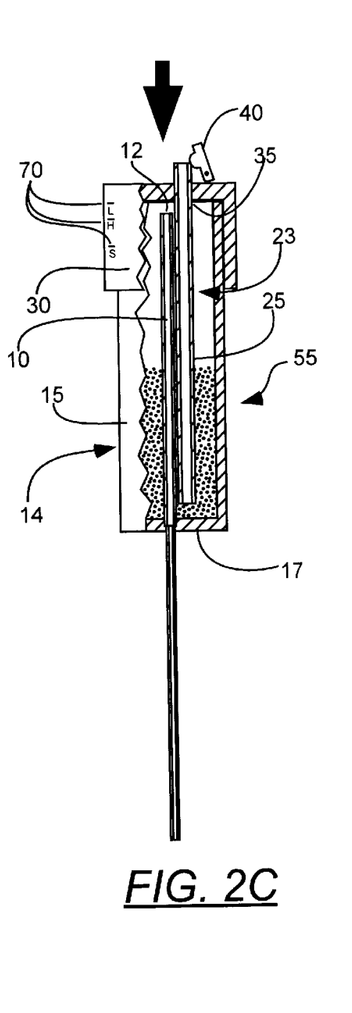

Referring to FIG. 2, once gas-delivery conduit 25 is in fluid communications with gas-receiving port 35, the position of closure cap 30 determines the distance to discharge conduit inlet 12. The gap between closure cap 30 and discharge conduit inlet 12 determines the gas-abrasive mixing and flow rate. Adjusting the gap between closure cap 30 and discharge conduit inlet 12 regulates these gas-abrasive flow characteristics. Regulator markings 70 are located on closure cap 30. Regulator markings 70 indicate the regulation setting on the device, where high abrasion power 'H' setting is for a wider gap than the low abrasion power 'L' setting.

Figure 3A:
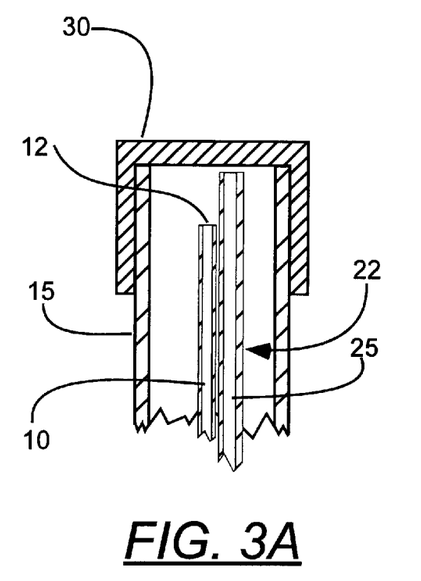
FIGS. 3A & 3B and FIGS. 4A & 4B show cross-sectional side views of alternative embodiments of the claimed device, where the closure cap is made of a compliant material with means for a gas-receiving port. The particulate matter and pressurized-gas source are omitted.
Figure 3B:
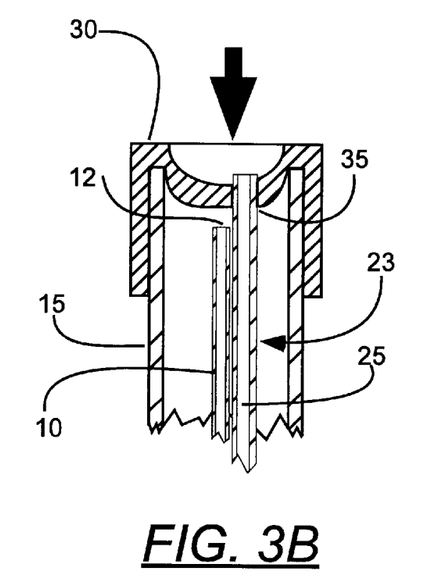
Figure 4A:
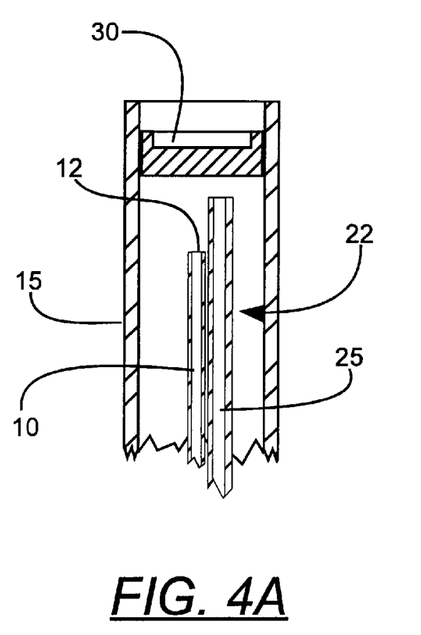
Figure 4B:
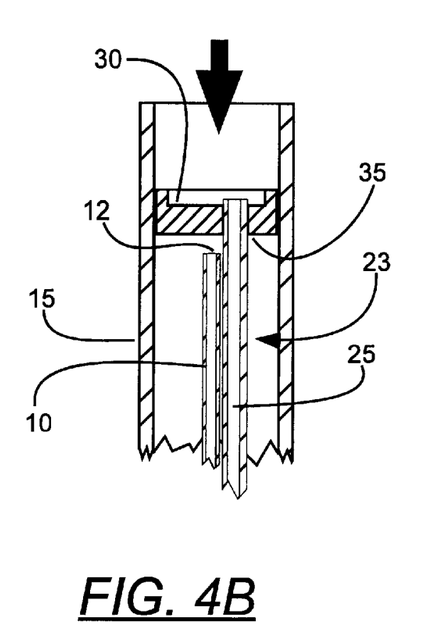

Although FIG. 1 and FIG. 2 depict one potential design for forming gas-receiving port 35, many other viable solutions exist. In FIG. 3 and FIG. 4, suffix A denotes closure cap 30 position for reservoir 22 and suffix B denotes closure cap 30 position for mixing chamber 23. Referring to FIG. 3, an alternate embodiment is presented for closure cap 30. In this embodiment, closure cap 30 is fabricated of a compliant material—such as rubber or silicon—that is penetrable by gas-delivery conduit 25. The compliance characteristic provides closure cap 30 the ability to form gas-receiving port 35 in fluid communications with gas-delivery conduit 25, as closure cap 30 is pushed over and penetrated by gas-delivery conduit 25.

This embodiment removes the need for gas-receiving port cap 40, since gas-receiving port 35 is only formed as gas-delivery conduit 25 punctures and protrudes through compliant closure cap 30. As compliant closure cap 30 is retracted, gas-delivery conduit 25 disengages closure cap 30 and gas-receiving port 35 is closed. Once gas-receiving port 35 is closed mixing chamber 23 is disabled. Thus, since gas can not be delivered into mixing chamber 23 it reverts back to form reservoir 22. For embodiments where gas-delivery conduit 25 abuts container side wall 15, the closure cap 30 compliant characteristic is used to surround gas-delivery conduit 25 to form gas-receiving port 35.

Referring to FIG. 4, a preferred embodiment is presented for closure cap 30. In this embodiment closure cap 30 is also fabricated of a compliant material; however, closure cap 30 is enclosed by container side wall 15. In this preferred embodiment, gas-delivery conduit 25 protrudes closure cap 30 to form gas-receiving port 35, as closure cap 30 is displaced along container side wall 15 toward container end wall 17. These embodiments are suitable for combining the displacement of closure cap 30 with the attachment of a pressurized-gas source connector to the device. Therefore these embodiments provide means for transforming sealed reservoir 22 into functional mixing chamber 23 with a single motion.

Figure 5A:
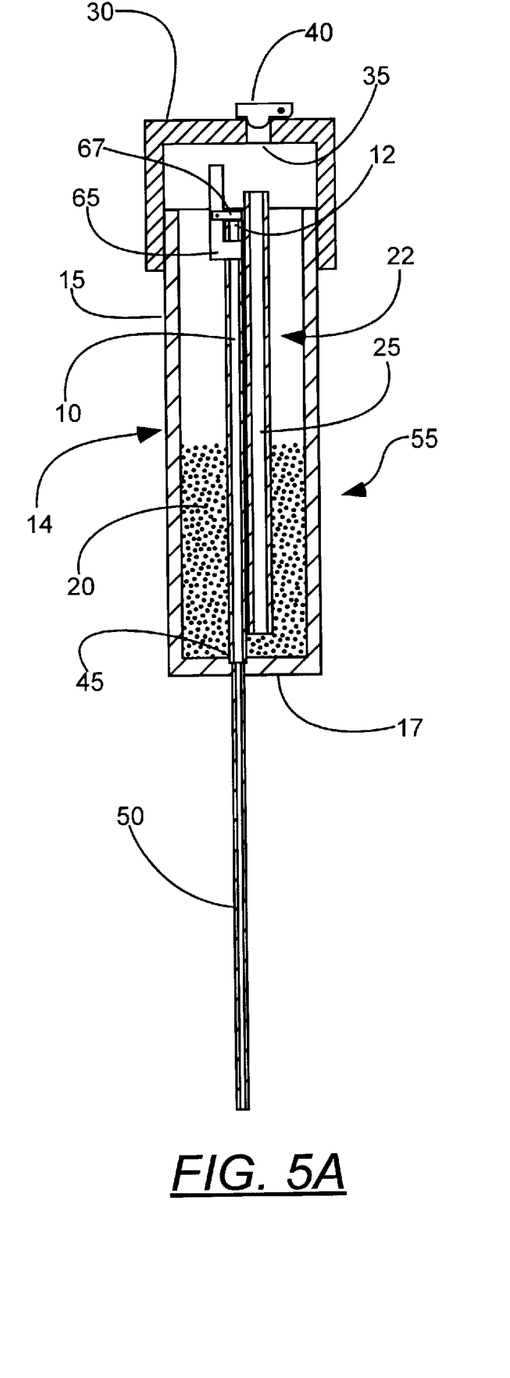
FIGS. 5A & 5B are a cross-sectional side view of the micro abrasive blasting device before and after the sealed reservoir is converted into a mixing chamber. The pressurized-gas source is omitted.

Referring to FIG. 5A, reservoir 22 is sealed by adding discharge conduit cap 67 to block discharge conduit inlet 12. A quantity of particulate matter 20 is sealed inside reservoir 22, since both gas-receiving port 35 and discharge conduit inlet 12 are hermetically capped.

Figure 5B:
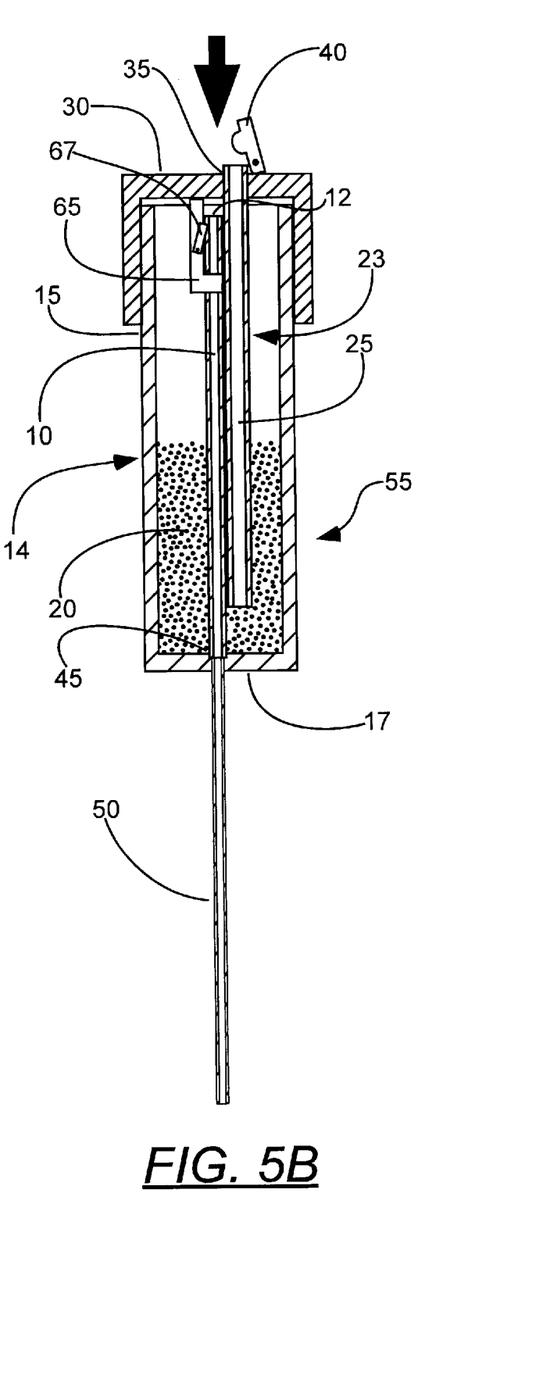

Referring to FIG. 5B, sealed reservoir 22 is converted into functional mixing chamber 23 by opening gas-receiving port 35 and discharge conduit inlet 12. The positioning of closure cap 30 so gas-delivery conduit 25 is in fluid communications with gas-receiving port 35, provides means for pressurized-gas to be delivered into mixing chamber 23. The removal of discharge conduit cap 67 so that discharge conduit inlet 12 is open, enables the gas-particulate mixture to enter discharge conduit 10.

A method is provided that accomplishes the unsealing of reservoir 22 and the formation of mixing chamber 23 without the need to remove closure cap 30. The method provides means for discharge conduit cap 67 to clear discharge conduit inlet 12 as closure cap 30 is positioned. FIG. 5A and FIG. 5B show the transformation of sealed reservoir 22 into mixing chamber 23 as closure cap 30 is positioned. Displacement of closure cap 30 causes discharge conduit cap mechanism 65 to slide along discharge conduit 10 towards discharge port 45. As discharge conduit cap mechanism 65 slides along discharge conduit 10 towards discharge port 45, discharge conduit cap 67 is removed from blocking discharge conduit inlet 12.

Figure 6A:
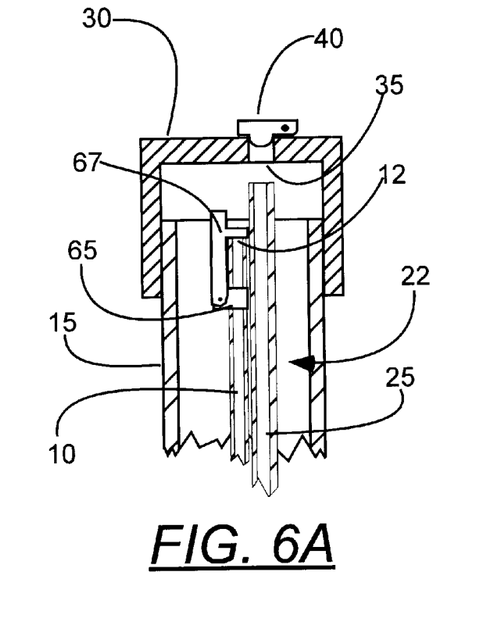
Figure 6B:
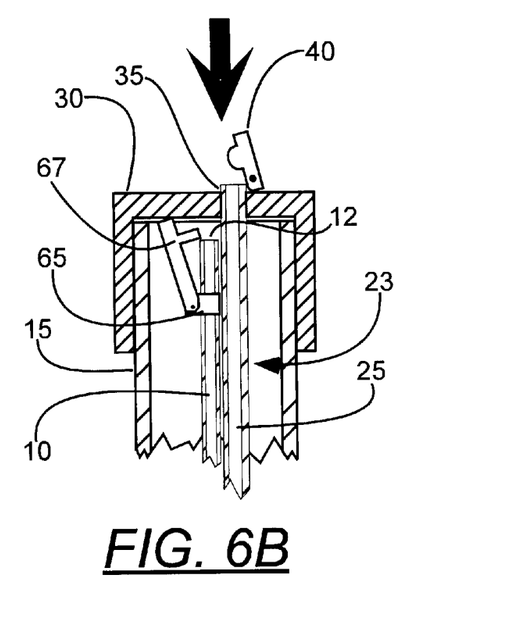
Figure 7A:
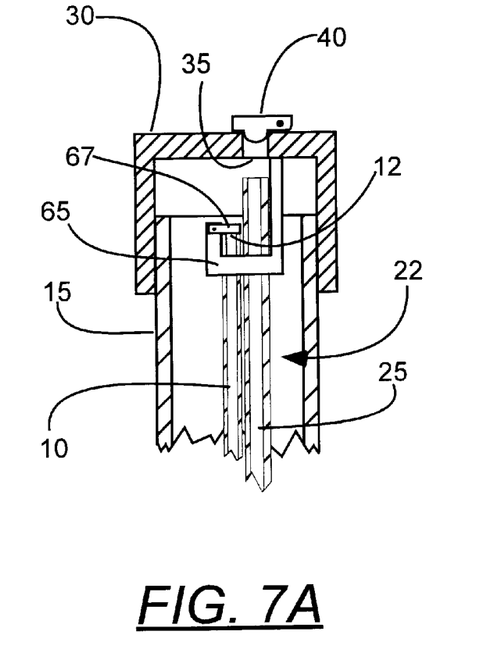
Figure 7B:
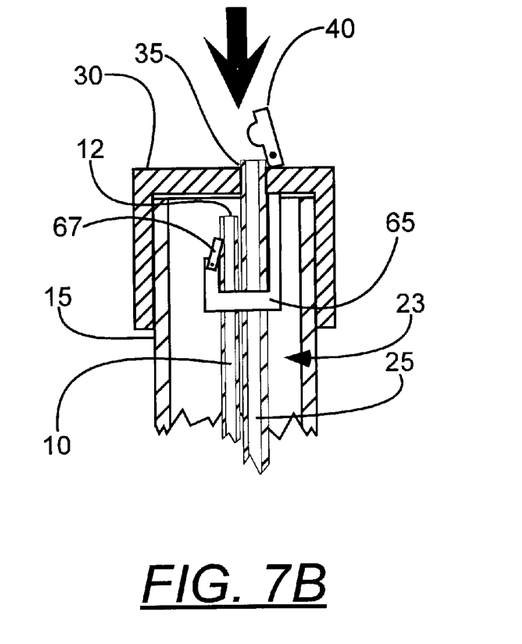
Figure 8A:
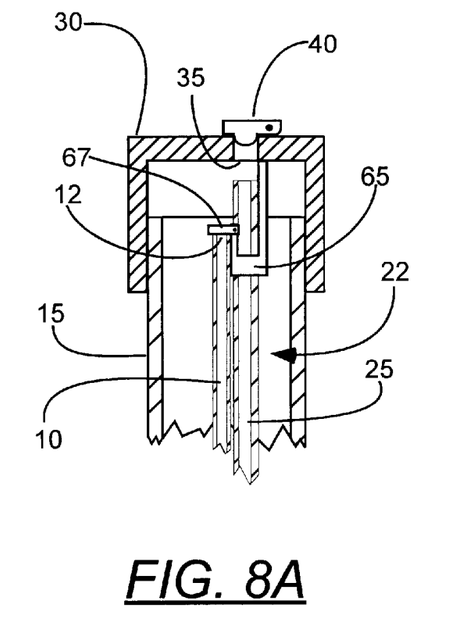
Figure 8B:
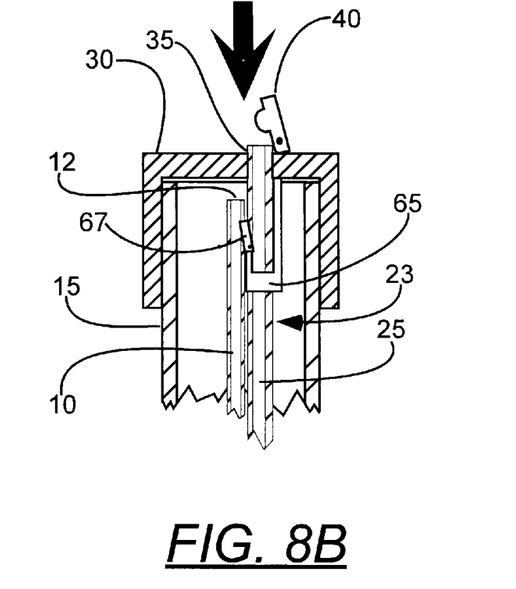

Other possible means of removing discharge conduit cap 67 from blocking discharge conduit inlet 12 are shown in FIG. 6, FIG. 7, FIG. 8, and FIG. 9. For these figures suffix A denotes closure cap 30 position for sealed reservoir 22 and suffix B denotes closure cap 30 position for mixing chamber 23. FIG. 6 show a discharge conduit cap mechanism 65 that is fixed with respect to discharge conduit 10, while discharge conduit cap 67 pivots away from discharge conduit inlet 12. FIG. 7 and FIG. 8 show embodiments where discharge conduit cap mechanism 65 is configured with gas-delivery conduit 25 instead of gas discharge conduit 10. These embodiments are advantageous in reducing the interference of the discharge conduit cap mechanism 65 with the gas flow patterns in the vicinity of discharge conduit inlet 12.

Figure 9A:
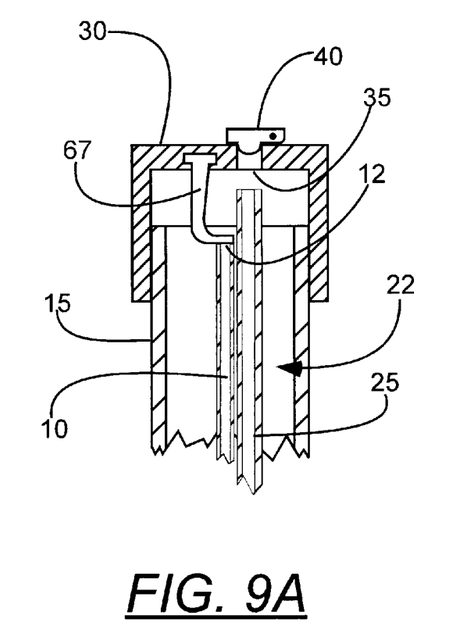
FIGS. 9A & 9B are cross-sectional side views of alternative embodiments of the claimed device, with means for capping the discharge conduit inlet internal to the sealed reservoir. The particulate matter and pressurized-gas source are omitted.
Figure 9B:
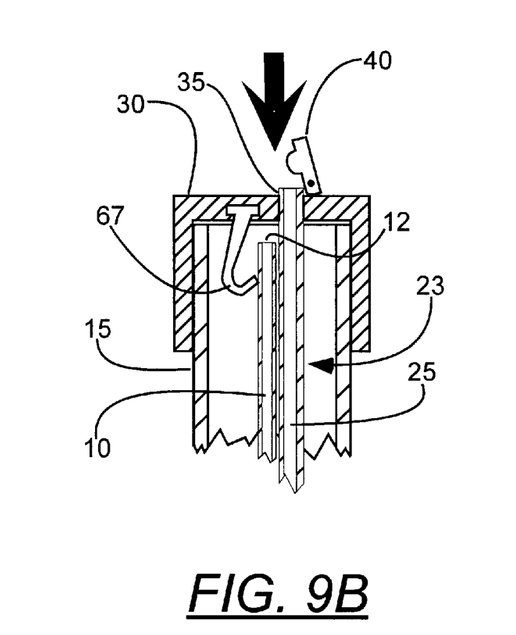

Although for the purpose of clarity discharge conduit cap mechanism 65 and discharge conduit cap 67 are described as two separate components, discharge conduit cap mechanism 65 and discharge conduit cap 67 can also be integrated into a single contiguous component. This single contiguous component can be fabricated from a flexible material that is sufficiently rigid to act as discharge conduit cap mechanism 65, yet compliant enough to flex as to achieve the movement of discharge conduit cap 67. In addition, as shown in FIG. 9, discharge conduit cap 67 can be attached to or integrated with closure cap 30 as a single contiguous component.

Figure 10A:
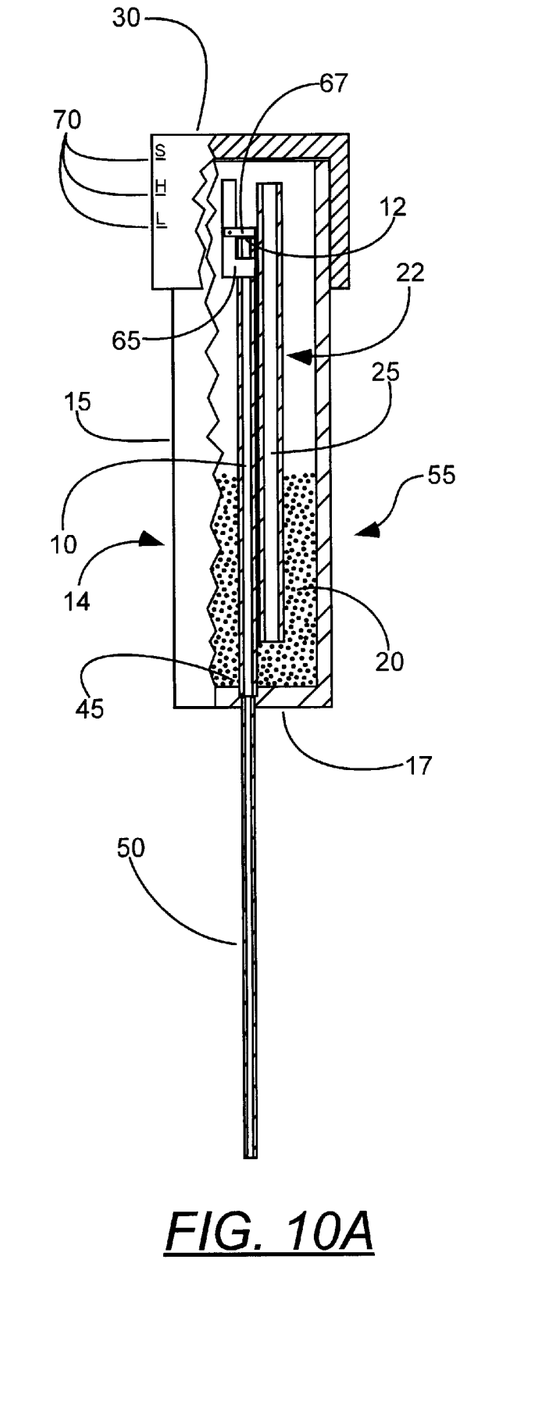
FIGS. 10A & 10B shows a cross-sectional side view of an alternative embodiment of the sealed micro abrasive blasting device, where the closure cap is made of a compliant material. The pressurized-gas source is omitted.
Figure 10B:
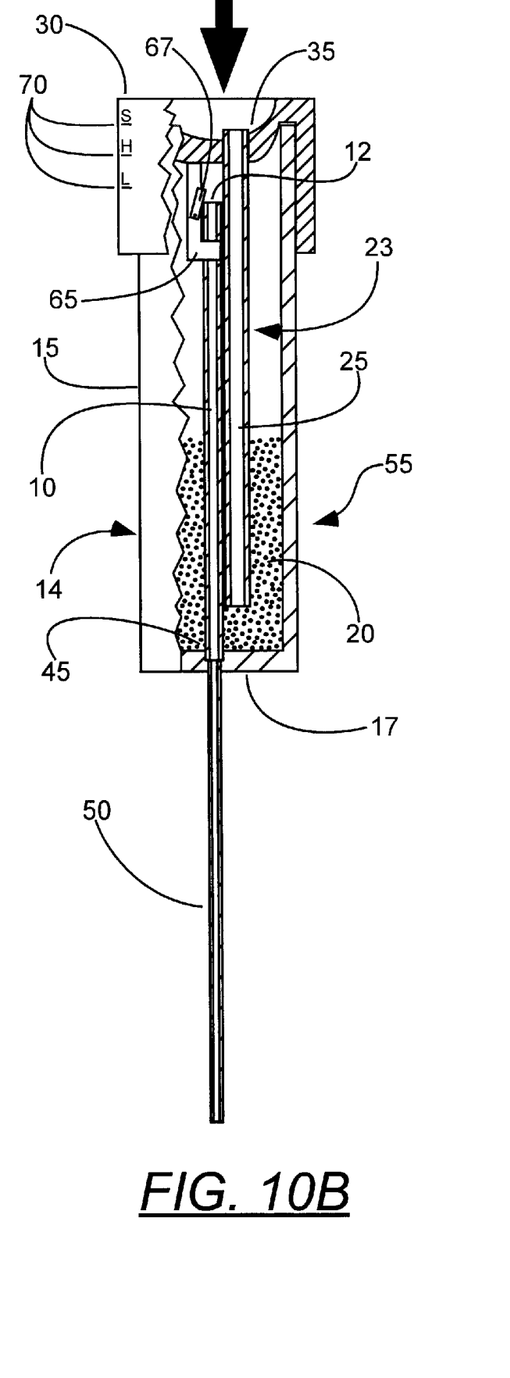
Figure 11A:
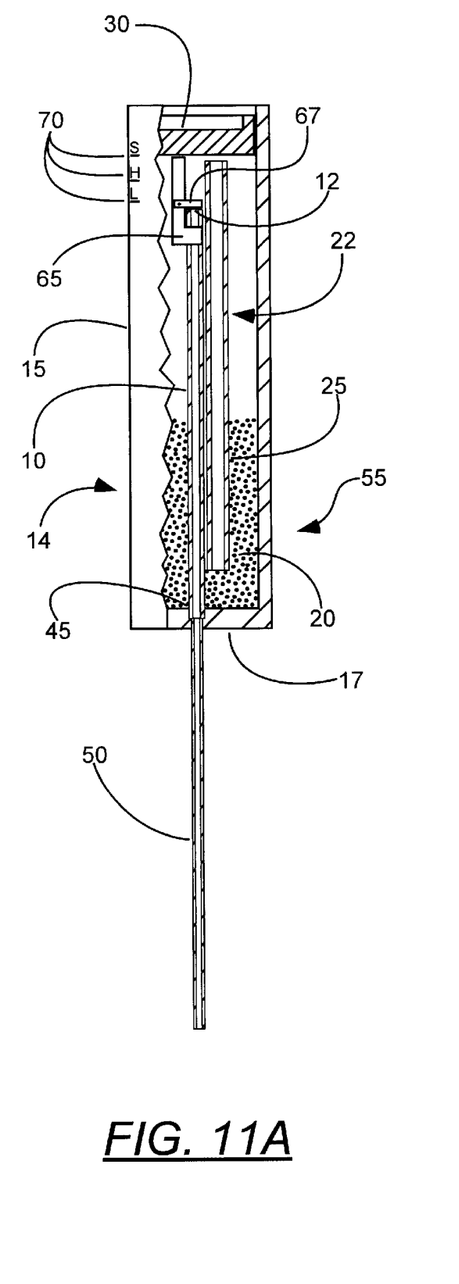
FIGS. 11A & 11B and FIGS. 12A & 12B are cross-sectional side and perspective views, respectively, of the preferred embodiment of the innovative device, where the closure cap is made of a compliant material and is enclosed by the container side wall. The particulate matter is omitted from FIGS. 12, while the pressurized-gas source is omitted from both FIGS.
Figure 11B:
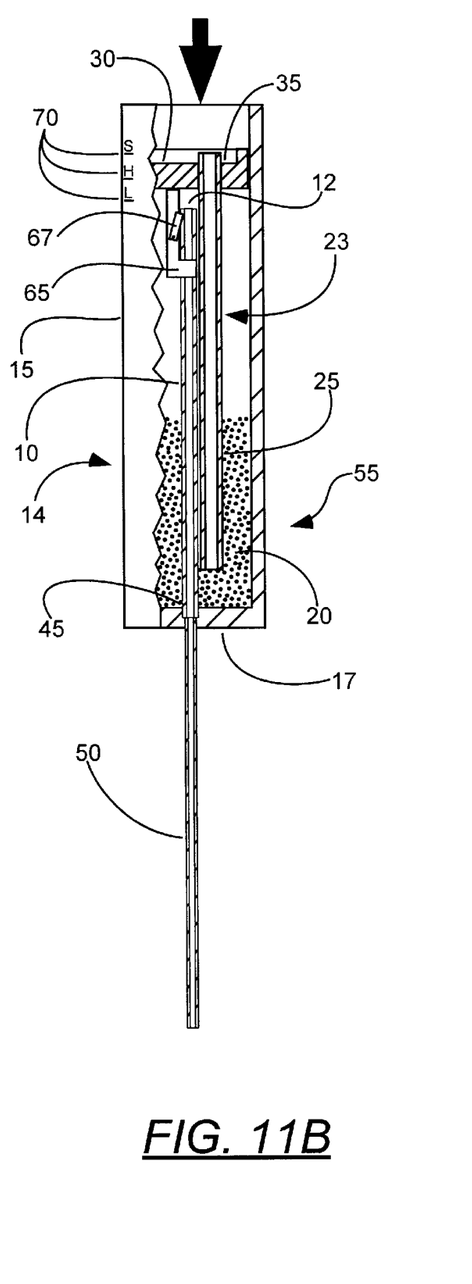
Figure 12A:
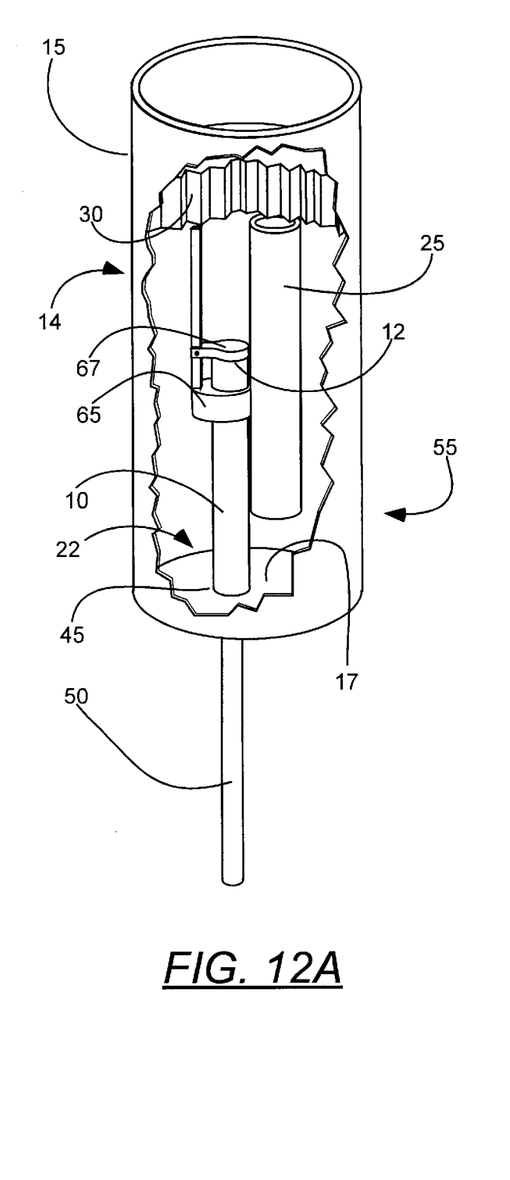
Figure 12B:
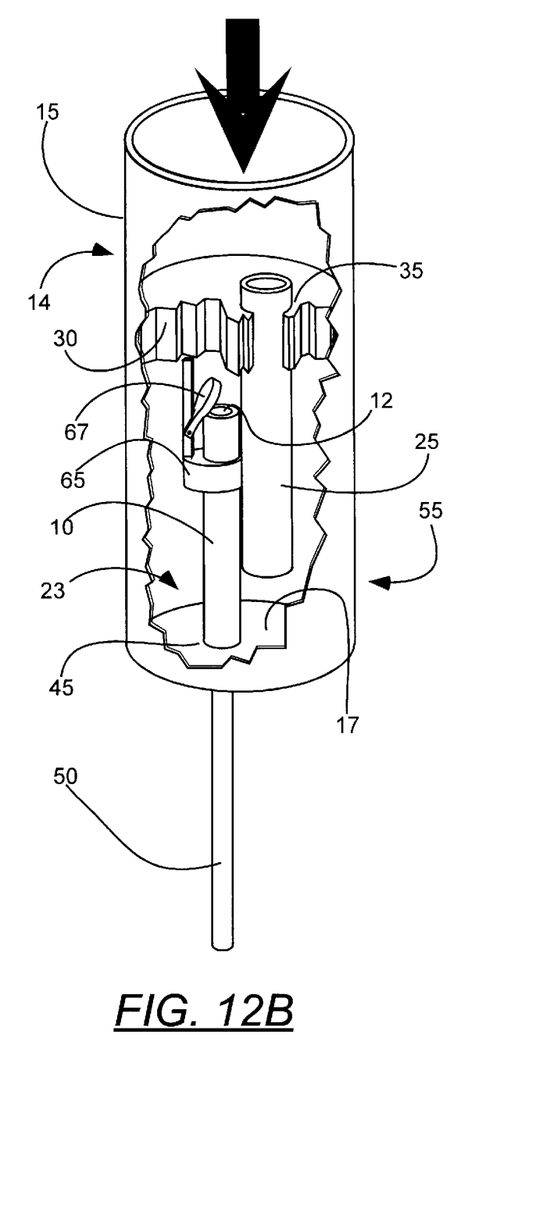

It is anticipated by the author that the disclosed embodiments and means for (I) disposing gas-delivery conduit 25 in sealed reservoir 22;

(II) implementing closure cap 30 with means for gas-receiving port 35; and (III) implementing discharge conduit cap 67 with means for clearing discharge conduit inlet 12,via displacement of closure cap 30, can be utilized in various combinations to form micro abrasive blasting device 55. FIG. 10 presents an embodiment of the innovative micro abrasive blasting device with a compliant closure cap 30 and discharge conduit cap 67. For the preferred embodiment shown in FIG. 11, regulator markings 70 are applied to the container side wall 15 instead of closure cap 30 to indicate the regulation setting. Regulator markings 70 also indicate closure cap 30 position for which the micro abrasive blasting device 55 is sealed 'S'. FIG. 12 provide a perspective view of the preferred embodiment.

From the description above, the following advantages of the present invention become evident:

(a) Providing a gas-delivery conduit located internal to the reservoir (I) eliminates the potential for deformation of the gas-delivery conduit during gas-delivery conduit insertion, and (II) eliminates the potential for clogging of the gas-delivery conduit during cap closure and device assembly.

(b) Providing the closure cap with means for a gas-receiving port (I) protects the abrasive material from adverse environmental conditions, while eliminating the need for a removable inlet cap, and (II) facilitates the displacement of the closure cap, thus providing means for regulating the gas-abrasive flow.

(c) Providing a cap at the discharge conduit inlet internal to the reservoir eliminates (I) the loss of abrasive material through the discharge conduit during abrasive filling;

(II) the potential for abrasive material to accumulate and bind the discharge conduit prior to use;

(III) the affects of adverse environmental conditions on the abrasive material; and (IV) the risk of the tip cap dislodging off the particle-directing tube when pressurized-gas is applied.

(d) Providing the discharge conduit cap internal to the reservoir, with means of clearing the discharge conduit inlet without the need to remove the closure cap, protects the integrity of the sealed reservoir.

(e) Providing a method for both the gas-delivery port and the discharge conduit inlet to open in a single motion makes the device extremely easy to setup for use.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

SUMMARY, RAMIFICATION, AND SCOPE

The present invention accomplishes the above-stated objectives, as well as others, as may be determined by a fair reading and interpretation of the entire specification.

Accordingly, the reader will see that the present invention is a superior micro abrasive blasting device with an integral sealed reservoir that converts into a functional mixing chamber. When not in use, the device forms a sealed reservoir that protects the stored particulate matter from contamination and spillage. When the device is setup for use, the sealed reservoir transforms into the operational mixing chamber central to the function of the device. The reservoir can be repeatedly refilled or pre-filled for single use applications. A method is provided for transforming the sealed reservoir into an operational mixing chamber in a single motion. Means are provided for regulating the gas-abrasive flow.

Furthermore, the present invention has the additional advantages in that it provides a more consistent device operation by locating the gas-delivery conduit internal to the container, thus eliminating the potential for gas-delivery conduit deformation during cap closure.

it provides a more reliable device by locating the gas-delivery conduit internal to the container, thus eliminating the potential for gas-delivery conduit clogging during gas-delivery conduit insertion.

it provides a spillage free device by blocking the particulate matter from entering the discharge conduit during abrasive filling.

it provides an operationally superior device by preventing particulate matter from entering the discharge conduit until the device is ready for use.

it provides a more reliable device by eliminating the potential for abrasive material to bind the discharge conduit.

it provides a safer device by assuring that the discharge conduit inlet cap can never escape the device.

it provides a more convenient device by locating the discharge conduit inlet cap internal to the reservoir, with means of clearing the discharge conduit inlet without the need to remove the closure cap.

it provides a more reliable device operation by providing the closure cap with means for a gas-receiving port, to protect the abrasive material from adverse environmental conditions.

it provides the device with a variable range of operation by providing means for regulating the gas-abrasive flow.

it provides a more convenient device by providing the closure cap with means for a gas-receiving port, thus eliminating the need for a removable inlet cap.

it provides a sealed device that unseals in a single motion as the pressurized-gas delivery connector is attached to the device.

Thus the scope of the invention should be determined by the appended claims and their legal equivalents, rather than by the examples given.

What I claim as my invention is:

1. A micro abrasive blasting device, comprising:
   a container having a side wall and an end wall;
   a closure cap with means for a gas-receiving port disposed at the open end of said container;
   a gas-delivery conduit disposed within the container with one end directed towards and extending near to said closure cap and the other end directed towards said container end wall;
   a discharge port in the container end wall;
   a discharge conduit disposed within the container and extending in fluid communication from said discharge port towards the closure cap;
   and an elongate particle-directing tube disposed external to the container, a proximal end of said particle-directing tube in fluid communication with the discharge port;
   whereby displacement of the closure cap provides means for engaging said gas-delivery conduit to said gas-receiving port.

2. The apparatus, according to claim 1, wherein:
   said gas-delivery conduit disposed within the container is attached to said discharge conduit.

3. The apparatus, according to claim 1, wherein:
   said gas-delivery conduit disposed within the container is contiguous with said discharge conduit.

4. The apparatus, according to claim 1, wherein:
   a discharge conduit cap seals said discharge conduit inlet located opposite the discharge port.

5. The apparatus, according to claim 1, wherein:
   said discharge conduit cap has means for clearing the discharge conduit inlet with displacement of the closure cap.

6. The apparatus, according to claim 1, wherein:
   the closure cap is enclosed by said container side wall.

7. The apparatus, according to claim 1, wherein:
   the closure cap is made of compliant material and is enclosed by said container side wall.

8. The apparatus, according to claim 1, wherein:
   the closure cap positioning provides means for gas-abrasive flow regulation.

9. The apparatus, according to claim 1, wherein:
   the displacement of the closure cap provides means for disengaging the gas-delivery conduit from the gas-receiving port.

10. A micro abrasive blasting device, comprising:
    a container having a side wall and an end wall;
    a closure cap with means for a gas-receiving port disposed at the open end of said container;
    a gas-delivery conduit disposed within the container with one end directed towards said closure cap and the other end directed towards said container end wall;
    a discharge port in the container end wall;
    a discharge conduit disposed within the container and extending in fluid communication from said discharge port towards the closure cap;
    a discharge conduit cap seals said discharge conduit inlet located opposite the discharge port;
    and an elongate particle-directing tube disposed external the container, a proximal end of said particle-directing tube in fluid communication with the discharge port.

11. The apparatus, according to claim 10, wherein:
    the closure cap is enclosed by said container side wall.

12. The apparatus, according to claim 10, wherein:
    the closure cap is made of compliant material.

13. The apparatus, according to claim 10, wherein:
    the closure cap is made of compliant material and is enclosed by said container side wall.

14. The apparatus, according to claim 10, wherein:
    said discharge conduit cap has means for clearing the discharge conduit inlet with displacement of the closure cap.

15. The apparatus, according to claim 10, wherein:
    the closure cap positioning provides means for gas-abrasive flow regulation.

16. A micro abrasive blasting device, comprising:
    a container having a side wall and an end wall;
    a compliant closure cap enclosed by said container side wall and disposed at the open end of said container;
    a gas-delivery conduit disposed within the container with one end directed towards said closure cap and the other end directed towards said container end wall;
    a discharge port in the container end wall;
    a discharge conduit disposed within the container and extending in fluid communication from said discharge port towards the closure cap;
    a discharge conduit cap seals said discharge conduit inlet located opposite the discharge port, with means for clearing the discharge conduit inlet with displacement of the closure cap;
    and an elongate particle-directing tube disposed external the reservoir, a proximal end of said particle-directing tube in fluid communication with the discharge port.

17. The apparatus, according to claim 16, wherein:
    the closure cap positioning provides means for gas-abrasive flow regulation.

18. A micro abrasive blasting device, comprising:
    a container having a side wall and an end wall;
    a closure cap with means for a gas-receiving port disposed at the open end of said container;
    a gas-delivery conduit disposed within the container and extending in fluid communication from said gas-receiving port towards said container end wall;

a discharge port in the container end wall;

a discharge conduit disposed within the container and extending in fluid communication from said discharge port towards the closure cap;

and an elongate particle-directing tube disposed external to the container, a proximal end of said particle-directing tube in fluid communication with the discharge port;

whereby displacement of the closure cap provides means for disengaging said gas-delivery conduit from the gas-receiving port.

19. The apparatus, according to claim 18, wherein:

the closure cap is made of compliant material with means to seal the gas-receiving port.

* * * * *